(12) United States Patent
McKale

(10) Patent No.: US 7,819,873 B1
(45) Date of Patent: Oct. 26, 2010

(54) METHOD AND APPARATUS FOR FIXATION OF SURGICAL INSTRUMENTS

(75) Inventor: James M McKale, Syracuse, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1728 days.

(21) Appl. No.: 10/946,530

(22) Filed: Sep. 21, 2004

(51) Int. Cl.
*A61B 17/56* (2006.01)

(52) U.S. Cl. ........................................................ 606/53

(58) Field of Classification Search ............... 606/53, 606/72–73, 79, 82, 86–87, 96, 300, 301, 606/308, 309, 310, 321; 411/356, 357
See application file for complete search history.

(56) References Cited

U.S. PATENT DOCUMENTS

| | | | | |
|---|---|---|---|---|
| 2,518,019 A | * | 8/1950 | Kane | 606/62 |
| 4,414,966 A | * | 11/1983 | Stednitz | 606/73 |
| 4,421,112 A | * | 12/1983 | Mains et al. | 606/88 |
| 4,796,877 A | * | 1/1989 | Musil et al. | 269/87.2 |
| 4,892,093 A | * | 1/1990 | Zarnowski et al. | 606/82 |
| 5,078,719 A | * | 1/1992 | Schreiber | 606/87 |
| 5,122,132 A | | 6/1992 | Bremer | |
| 5,375,956 A | * | 12/1994 | Pennig | 411/389 |
| 5,562,671 A | | 10/1996 | Goble et al. | |
| 5,643,268 A | * | 7/1997 | Vilsmeier et al. | 606/73 |
| 5,672,178 A | | 9/1997 | Petersen | |
| 6,203,544 B1 | | 3/2001 | Gotzen | |
| 6,371,124 B1 | | 4/2002 | Whelan | |
| 6,635,059 B2 | * | 10/2003 | Randall et al. | 606/73 |
| 6,923,648 B1 | * | 8/2005 | Rassoli | 433/173 |
| 2003/0216780 A1 | | 11/2003 | Fitts et al. | |

* cited by examiner

*Primary Examiner*—Eduardo C Robert
*Assistant Examiner*—David Comstock
(74) *Attorney, Agent, or Firm*—Harness, Dickey

(57) ABSTRACT

A fixation pin, surgical assembly and method of fixing a cutting guide to a bone. The fixation pin includes a body having an interference portion which engages the wall of a hole in bone, a tip and a tool mating section. The surgical assembly includes an instrument for engaging the selected bone and a fixation pin operably interconnected with the instrument to engage the selected bone. Methods of fixing an instrument with a fixation pin are included. An incision is made to expose a bone. The instrument and fixation pin are interconnected and the assembly is mounted relative to a surgical site. The fixation pin is positioned in a rotationally fixed manner at a select position relative to the instrument to hold the instrument against the bone.

3 Claims, 3 Drawing Sheets

METHOD AND APPARATUS FOR FIXATION OF SURGICAL INSTRUMENTS

FIELD OF THE INVENTION

The present invention relates to fixation and cutting instruments. More particularly, the present invention relates to a fixation pin for use in knee arthroscopic surgical procedures.

BACKGROUND OF THE INVENTION

During arthroplasty procedures, the implant region is generally prepared by shaving or resecting segments of the bone. In knee replacement surgery, a proximal portion of the tibia and a distal portion of the femur are generally resected to be sized to receive the implant. Cuts are made using various saws, drills or other grinding or shaving tools.

To assist in resection, surgical guides may be used with the saw to ensure that the cut angles and dimensions conform to the implant. Various techniques require the sequential use of a single surgical guide, such as a cutting block, or several surgical guides to make a plurality of cuts in a plurality of dimensions and angles. For example, a cutting block or guide may be used to engage the distal portion of the femur to resect the bone to receive the femoral portion of the knee implant. Subsequently, the same or a different cutting block may be used to engage the proximal portion of the tibia to resect the bone to receive the tibial portion of the knee implant. Therefore, it may be beneficial to have an easily repositionable cutting block.

Along with having an easily repositionable cutting block, it is sometimes desirable to have the cutting block remain stationary during portions of or throughout the selected resection even while the saw or drill is vibrating or oscillating. An unplanned movement of the cutting block may result in saw shifting and an improper bone resection being made, which may impact the fit and function of the implant.

As a further surgical supplement to the cutting guides, fixation pins may be used. The fixation pin may be interconnected with the cutting guide and the bone through a drilled hole or tunnel in the bone to make the cutting block generally immobile while the saw is vibrating. After the desired cut has been made, the fixation pin and the cutting guide are removed. Depending on the type of cutting guide used and the extent or quantity of resections made during the procedure, the cutting guide and fixation pin may be used in several locations during the procedure.

It may be desirable to have a fixation pin that provides enhanced fit in the bone and enhanced security of the cutting guide to a bone region while performing a selected procedure.

SUMMARY OF THE INVENTION

Embodiments of the present invention relate to fixation pins. The pin includes a body comprising a distal end, a proximal end and an interference portion; a tip at the distal end of the body; and a tool mating section at the proximal end of the body. The fixation, pin engages a hole in bone which extends along a first longitudinal axis and the fixation pin body extends along a second longitudinal axis such that the interference portion engages an inner wall of the bone hole or extends beyond a cross section of the bone hole taken substantially perpendicular to the first longitudinal axis. The body cross section along the second longitudinal axis is substantially constant along its length. The fixation pin may further include a tapered section between the body and the tool mating section. The body may have a diagonal greater than the diameter of the distal end. Additionally, the tapered section may have a diagonal greater than the diagonal of the body. The tool mating section may contain threads adapted to mate with a tool.

Various surgical assemblies for attaching an instrument to bone are also provided. A surgical assembly includes an instrument for engaging the selected bone and a fixation pin operably interconnected to the instrument to engage the selected bone and hold the selected instrument at a selected position relative to said bone in a rotationally fixed manner. The surgical assembly may also include an instrument with a saw guide for guiding a saw blade relative to the bone. The instrument may be selectively affixed for the duration of a selected procedure and removed only at a selected time. Optionally, the fixation pin may be substantially removably fixed relative to the instrument to allow for fixing, adjusting and subsequent removal of the instrument during a surgical procedure. Exemplary instruments used may include a tibial cutting guide, femoral cutting guide, humeral cutting guide and combinations thereof.

Various methods according to embodiments of the present invention include a method of fixing an instrument with a fixation pin at a selected position relative to a surgical site. The methods include exposing a bone; creating a hole in the bone, the hole having a first cross-section shape; providing the fixation pin having a second cross-section shape that is substantially constant along a bone-engaging surface of the pin; interconnecting the instrument and the fixation pin; mounting the instrument relative to the surgical site; positioning the fixation pin in a rotationally fixed manner at a selected position relative to the instrument; and holding the instrument with the fixation pin. The method may include guiding a second instrument to perform a selected procedure. The method may also include resecting a portion of bony tissue. Interconnecting of the instrument and the fixation pin may include substantially fixing the fixation pin to the instrument in a substantially immovable fashion or substantially movably fixing the fixation pin to the instrument such that the selected instrument is movable relative to the fixation pin.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the various embodiment(s) is merely exemplary in nature and is in no way intended to limit the invention, its application, or uses. Although various embodiments may be illustrated in conjunction with a square fixation pin or a cutting block, it is understood that the fixation pins, surgical kits and methods of this invention may be of any appropriate shape and may be used with any appropriate instruments. It will be further understood that although various embodiments may relate to any appropriate procedure and not solely the illustrative use in conjunction with knee arthroplasty.

Figure 1:
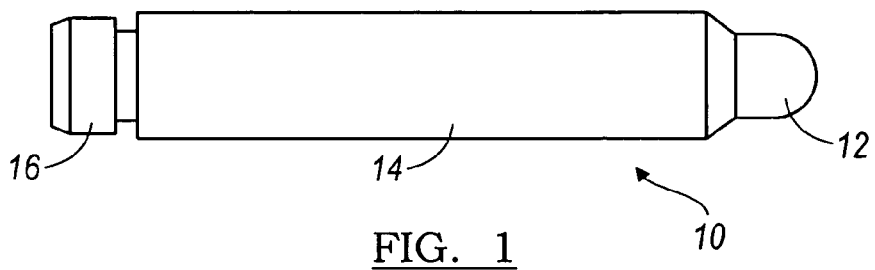
FIG. 1 depicts a side view of a fixation pin according to various embodiments.

As depicted in FIG. 1, a fixation pin 10 comprises a tip 12, a body 14 having an interference portion 15, and a tool mating section 16. The tip 12, the body 14 and the tool mating section 16 may be substantially concentric and generally aligned about a common axis. The tip 12 is at the distal end of the body 14 and the tool mating section 16 is at the proximal end of the body 14. The fixation pin 10 may be made of any biocompatible material, metal or alloy. In various embodiments, the fixation pin 10 is made of stainless steel or a cobalt chrome alloy such as F562.

The fixation pin 10 may be placed in a space in the bone such as a drilled hole or a bone tunnel 17. As depicted, the bone tunnel 17 is round. The bone tunnel 17 may also be a square, rectangle or oval opening formed by punching the shape into the bone. Fixation pins, surgical kits and methods of this invention may be used with any suitable opening shape that provides a press or interference fit.

The tip 12 may be a blunt tip, a conical tip or a bullet nose tip. The tip 12 is depicted as a bullet nose which is a rounded or cylindrical tip having a smooth surface. The tip 12 may be free from points or sharp corners. Having a rounded and smooth tip facilitates insertion of the fixation pin 10 into the bone tunnel 17. The smooth nose may eliminate the potential glove or skin puncture experienced by users of fixation pins with sharp pointed tips and prevents the inadvertent skin puncture of the patient in whom the pin is being inserted. While the depicted fixation pin 10 contains a smooth tip 12, the tip 12 may also be threaded, notched, chamfered or otherwise contain non-smooth features. The tip 12 may have a uniform diameter or it may have a series of increasing diameters. For example, the tip 12 may taper and have a maximum diameter located at the distal end of the body 14. It is beneficial if the maximum tip 12 diameter is sufficiently small to fit into the bone tunnel 17.

The body 14 may be of any shape. Body 14 types may include circles, ellipses or polygons such as triangles, tetragons, pentagons, hexagons, heptagons, octagons, ennagons, decagons, hendecagons, dodecagons, the n-gons (polygons with greater than thirteen sides) and etc. The body may be a cyclic polygon such that all vertices lie within a circle or it may have an irregular shape. The body 14 may be a circle, oval, curve, free-form or other non-polygon shape. It is generally desirable to have the shape of the body 14 facilitate use with the bone and with limitations of other instruments (i.e.: diameter of the instrument openings).

Figure 2:
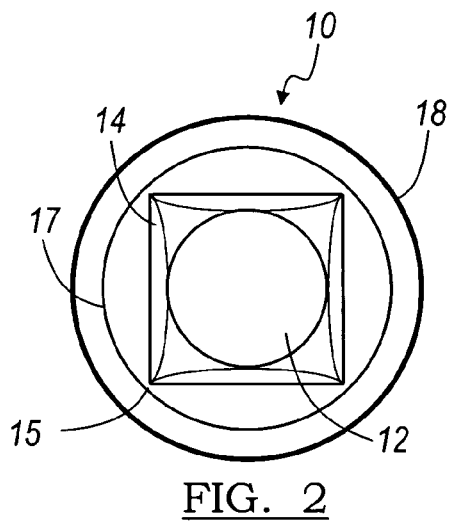
FIG. 2 depicts a front view of a fixation pin according to various embodiments.
Figure 3A:
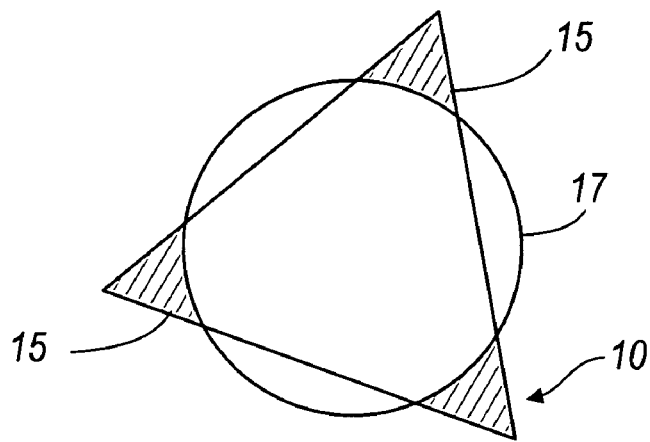
FIG. 3a-c depict alternate shapes of the fixation pin according to various embodiments.
Figure 3B:
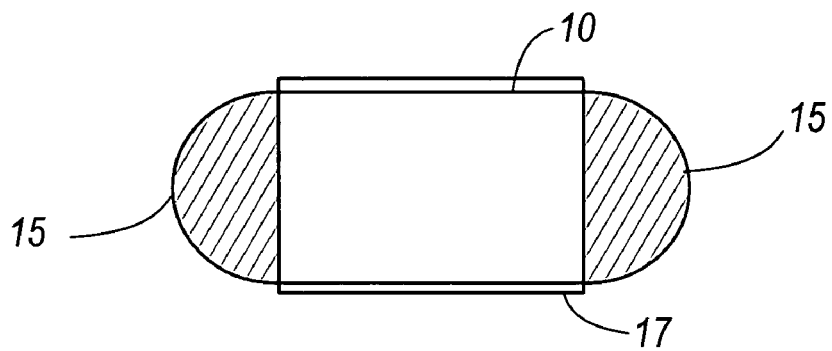
Figure 3C:
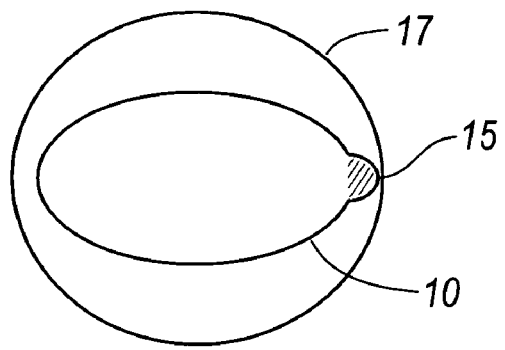

The body 14 includes an interference portion 15. The interference portion 15 is an integral part of the body 14 such that the cross section can be constant across the length of the body 14. The interference portion 15 may extend beyond the cross-section of the bone tunnel 17 to cut into and provide a secure interference fit of the body 14 at single contact point or a plurality of points. As depicted in FIG. 2, the square body 14 includes four corners which serve as the interference portions 15. The illustration of the square body 14 having corners serving as interference portions 15 is for simplicity and not intended to be limiting. Other polygon or other shaped pins 10 having multiple interference portions 15 as an integral part of the body 14 are depicted in FIGS. 3a and 3b, respectively. Various embodiments include non-polygon shaped pins 10, depicted in FIG. 3c as an oval. In such an embodiment, the interference portion 15 may be a protrusion or bump on the body 14 where the interference portion 15 extends only to the bone tunnel 17 wall thereby providing the interference fit. The protrusion may include tips, blunt ends, corners or curves. It may be desirable to combine a polygon shaped body 14 with such a protrusion type interference portion 15. For example, a hexagon shaped body 14 may include a rounded protrusion as the interference portion 15 such that the corners of the hexagon do not engage the bone tunnel 17.

Returning to FIG. 1, the distal end of the body 14 is joined to the tip 12. Depending on the combination of shapes, the tip 12 and the body 14 may appear concentric when viewed from the front, as depicted in FIG. 2. The body 14 may have a diagonal greater than the diameter or any cross-section length of the tip 12. The tip 12 guides the pin 10 into the bone tunnel 17 and the body 14 provides a press fit against the bone by engaging interference portion(s) 15 with one or more points along the perimeter of the bone tunnel 17.

Returning to FIG. 1, the tool mating section 16 is adapted to receive a tool for use in inserting the fixation pin 10 and may define any appropriate element. The tool mating section 16 may be externally or internally threaded to engage a tool having the mating thread pattern. Other suitable mating sections may include a shaped piece to fit a tool, for example, a hexagon shaped head for use with a wrench or socket type device or a Philips head screwdriver. The tool mating section 16 may also be void of any threads, formed shapes or indentations and may include a flat region suitable for impacting or hammering the fixation pin 10 into place. It is understood that while the tool mating section 16 is adapted to receive a tool, the fixation pin 10 may be inserted without a tool by using hand pressure or manipulation. In such embodiments, the tool mating section 16 may include a handle or any appropriate mechanism that allows for manipulation of the fixation pin 10 either by a single hand or both hands of a user of the fixation pin 10.

Figure 4:
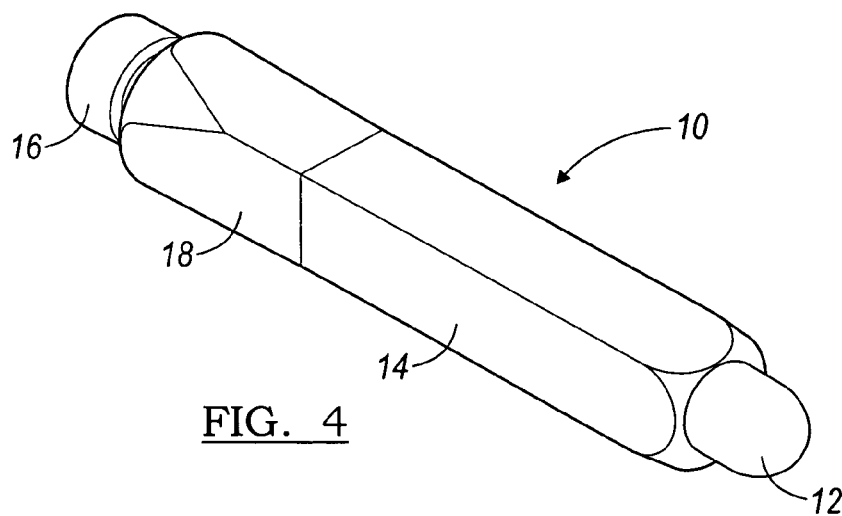
FIG. 4 depicts a perspective view of a fixation pin according to various embodiments.

Referring to FIG. 4, the fixation pin 10 further includes a tapered section 18 between the body 14 and the tool mating section 16. The tapered section 18 may share a common axis with the tip 12, the body 14 and the tool mating section 16. Generally, the tapered section 18 begins with the body 14 and radially diverges or "flares out" towards a base. As depicted, the tapered section 18 begins as a square and radially diverges towards the base. The base may be any appropriate shape that provides a radial divergence from the body 14 and causes the tapered section 18 to flare out. For example, the base may either be a square having a larger diagonal than the body 14 or a circle having a diameter larger than the body 14 diagonal. The tapered section 18 and the body 14 may be of the same shape (square and square as depicted) or may be of any combination of shapes such as a pentagon body 14 combined with an octagon tapered section 18 or a substantially oval shape with single interference portion 15 comprising the body 14 combined with a triangular tapered section 18. FIG. 2 shows the front view of the fixation pin 10 having such a flare out where the tapered section 18 terminates in a circle having a diameter larger than the body 14 diagonal. The tip 12 is of a smaller diameter than the longest diagonal of the body 14 which is in turn smaller than the flare of the tapered section 18.

The tapered section 18 provides supplemental press fit to the press fit from the body 14. Similar to the action of the body 14, the shape of the tapered section 18 is a misfit for the bone tunnel 17 and provides a tight and secure engagement of the corners of the square tapered section 18 with the perimeter of the bone tunnel 17. The radially diverging form of the tapered section 18 provides increased resistance and press fit traversing the radial divergence towards the base and prevents the fixation pin 10 from loosening. The fixation pin 10 may be inserted at a sufficient depth such that part of the tapered section 18 also engages the bone. The tapered section 18 may also be of the same diameter as the bone tunnel 17 opening wherein when the fixation pin 10 is inserted into the bone tunnel 17, the body 14 and the entirety of the tapered section 18 engage the bone while the tool mating section 16 is the only region not contacting the bone.

In addition to enhancing press fit, the tapered section 18 also provides a protective block or cap to maintain the integrity of the insertion point and tunnel. Fitting the square, as depicted, or a shape with any interference portion 15 into a uniform bone tunnel 17 produces small gaps or spaces where the perimeter of the body 14 does not match with the circular measurements of the bone tunnel 17. These small gaps or spaces potentially serve as entry points for surgical debris or small particles released while using tools in conjunction with surgery. The flare out of the tapered section 18 is a barrier or cap thereby limiting exposure of the bone tunnel 17 to these particles and also "caps off" the pin opening of a mating instrument. To increase the barrier properties of the fixation pin 10, the base of the tapered section 18 may have a surface area larger than the surface area of the bone tunnel 17 opening.

The fixation pin 10 may be inserted using a tool suitable to cause impaction of the fixation pin 10 into the bone such as a hammer. As stated above, the tool mating section 16 may also be designed such that a suitable tool would be a wrench or socket type device. In such embodiments, the tool may be engaged (by turning, cranking, pressing a lever, etc.) to in turn impact the fixation pin 10 into the bone. The fixation pin 10 is removed such that the body 14 and the tapered section 18 are not rotated. In addition to the tool mating section 16 corresponding tool, pliers, clamps or a wrench type devices may be employed to grab the tool mating section 16 and pull the fixation pin 10 from the bone. As stated above, the fixation pin 10 may also be removed by the hands of the user without a tool.

Figure 6:
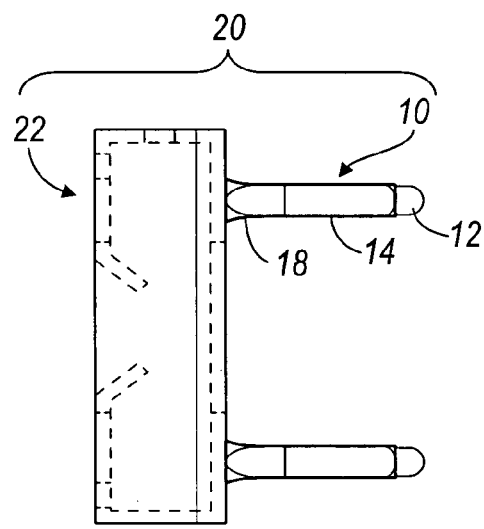
FIG. 6 depicts a side view of a surgical assembly or system according to various embodiments.
Figure 5:
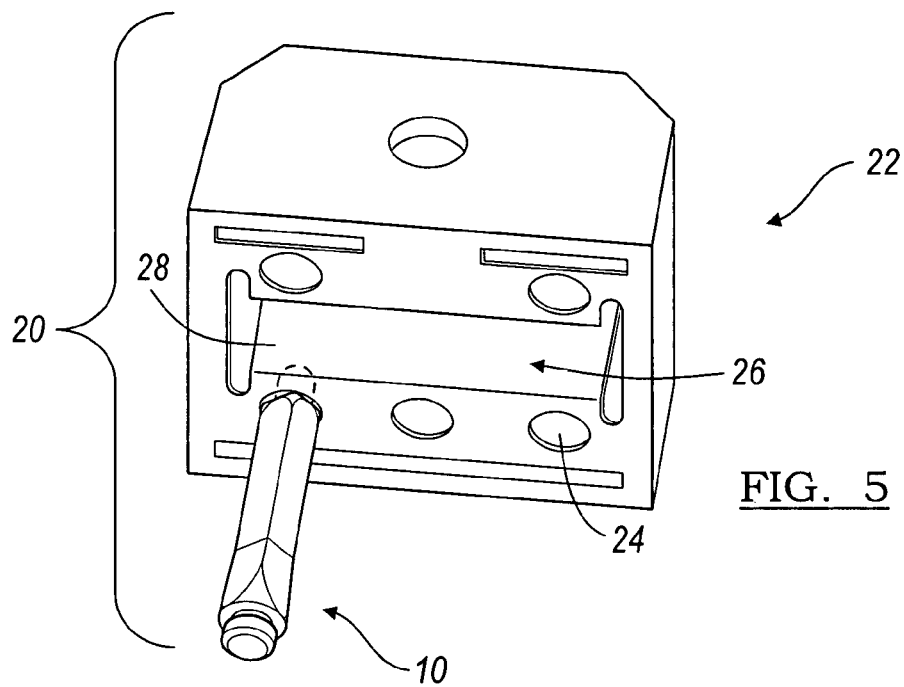
FIG. 5 depicts a perspective view of a surgical assembly or system according to various embodiments.

Referring to FIG. 5, embodiments of the present invention include a surgical assembly 20 for attaching an instrument to a selected bone. The surgical assembly 20 comprises an instrument, depicted as cutting block 22, for engaging the selected bone and a fixation pin 10 operably interconnected to the instrument through a pin hole 24 to engage the selected bone. The fixation pin 10 is able to hold the instrument in a rotationally fixed manner at a selected position relative to the selected bone. The surgical assembly 20 may contain the fixation pin 10 separate from the cutting block 22. As shown in FIG. 6, the assembly 20 may also include the fixation pin 10 being pre-attached to the cutting block 22 by welding, chemical adhesives, press fit, pinning or any other suitable means.

Returning to FIG. 5, the instrument may include any appropriate surgical instrument or tool. As depicted and for exemplary purposes alone, the instrument is a cutting block 22. The cutting block 22 may be a tibial cutting guide, a femoral cutting guide, a humeral cutting guide, etc. and combinations thereof. The cutting block 22 may, in addition, include any selected portions, such as a retractor engaging portion to retract a soft tissue relative to the cutting block 22.

The pin holes 24 in the cutting block 22 may be used to fix the cutting block 22 to a selected anatomical portion, such as a bone, using the fixation pin 10 described herein. The pin holes 24 may be of a smaller, larger or the same diameter as the bone tunnel 17 drill holes. In various embodiments, the pin holes 24 are of a sufficient diameter to facilitate passage of the fixation pin 10 through the pin hole 24 and to allow the interference portion 15 to engage the bone without obstruction. The pin hole 24 may be of a diameter which is less than the longest diameter of the tapered section 18 such that the tapered section 18 region closest to the body 14 engages the bone and the section closets to the tool mating section 16 engages the cutting block 22. The cutting block 22 may include other bone or tissue connecting portions, such as a second peg or additional threaded portions, such as screws. The fixation pin 10 may be inserted into the pin holes 24 before or after positioning the cutting block 22 relative to the surgical site.

The cutting block 22 further defines a guide passage or slot 26. The guide passage 26 includes a guide surface 28 that is operable to engage a selected tool, such as a saw, described further herein. The guide surface 28 allows for a substantially consistent resection of a selected bony portion by providing the instrument along the guide surface 28. It will be understood, however, that if the instrument block is not a cutting block then the guide surface 28, and other selected portions, may not be provided. It will be understood that the instrument block 22 may also include other appropriate portions, such as a drill guide, an impaction guide, and other appropriate or selected instruments that require attachment to any bone.

Figure 7:
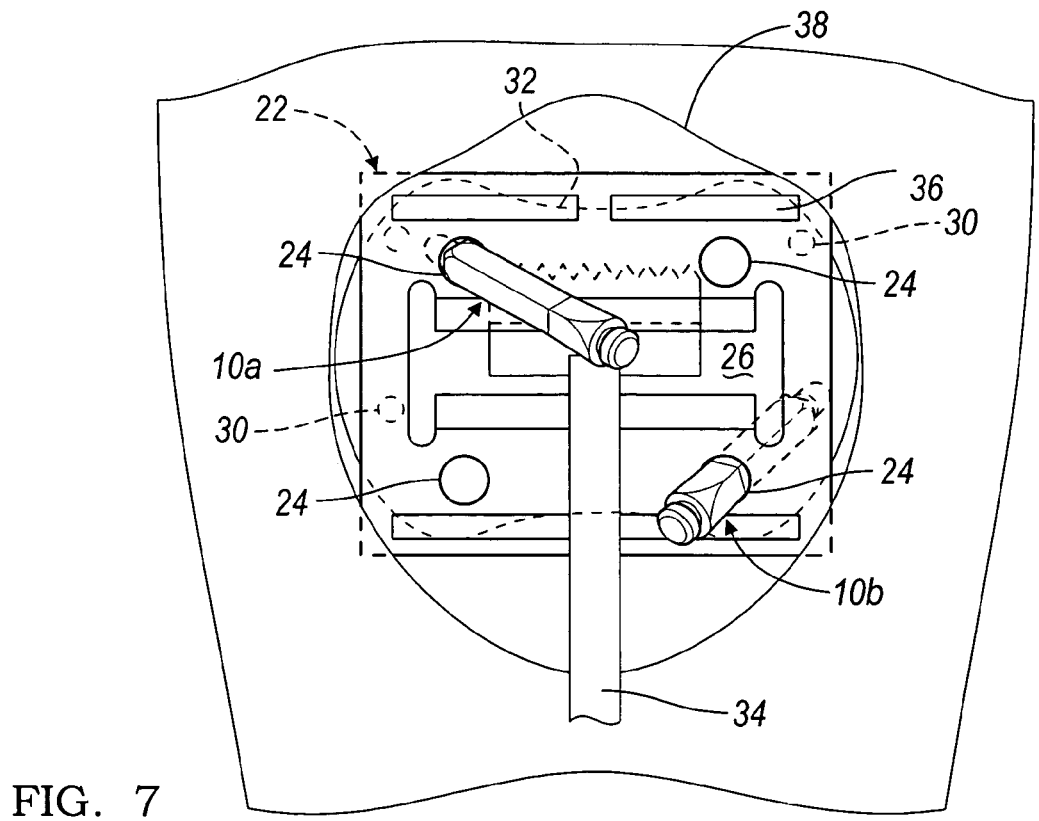
FIG. 7 depicts an environmental view of an exemplary use of a fixation pin according to various embodiments.

Referring to FIG. 7, the present invention also provides methods of fixing a cutting block 22 at a selected position relative to a surgical site with a fixation pin 10. An incision 38 is made to expose the bone. The cutting block 22 is then interconnected with the fixation pin 10. It is understood that the cutting block 22 may be mounted in the wound site and then the fixation pin 10 is inserted into or interconnected with the pin hole 24. Alternatively, the fixation pin 10 is interconnected with a pin hole 24 and then the associated system is mounted in the wound site. The cutting block 22 may be mounted onto the surgical site using a single fixation pin 10 or a plurality of fixation pins. The number of fixation pins 10 used in the particular system depends on the design of the cutting block 22 and the number of pin holes 24 provided therewith. As depicted, the cutting block 22 has four pin holes and utilizes two fixation pins 10a and 10b to secure the cutting block 22. The cutting block 22 may be affixed to a selected anatomical portion such as the distal end of a femur 32. The femur 32 may be resected for any appropriate purpose, such as for fitting of a selected distal femoral component for replacement of a portion or a total knee.

A second instrument such as a saw 34 may be guided by the cutting block 22 through the guide passage 26. Additional saws or instruments may be inserted and used with other guide passages such as passage 36. While using the saw, the cutting block 22 remains stationary with the press fit provided by the fixation pins 10a, 10b. The selected bone, quantity may be resected without slippage of the cutting block 22 due to the oscillation and vibrating of the saw 34. For example, the distal portion of the femur 32 may be resected at the proper size and angles to receive the selected distal femoral component.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical assembly for use in attaching to a selected bone defining a hole extending along a first longitudinal axis, comprising:
   a. an instrument for engaging said selected bone; and
   b. a fixation pin having a substantially smooth outer surface and being operably interconnected to said instrument comprising:
      i. a square body extending along a second longitudinal axis between a distal tip and a tapered section, the square body having:
         1. a distal end adjacent said distal tip;
         2. a proximal end; and
         3. an interference portion which extends beyond a cross section of said hole taken substantially perpendicular to the first longitudinal axis;
      ii. the tapered section having a first end at the body proximal end and a second end, wherein the tapered section has a first cross-sectional shape at said first end and a second cross-sectional shape at said second end, said first and second cross-sectional shapes being different, and wherein the tapered section increases constantly from the first end to the second end such that a diagonal of said second cross-sectional shape at said second end is greater than a diagonal of said first cross-sectional shape at said first end; and
      iii. a tool mating section adjacent said tapered section second end, wherein said fixation pin is substantially smooth along its entire length and further wherein said fixation pin holds said instrument at a selected position relative to said selected bone.

2. The surgical assembly according to claim 1, wherein said tapered section first cross-sectional shape at said first end is a square shape and said tapered section second cross-sectional shape at said second end is a circular shape.

3. The surgical assembly according to claim 1, wherein said tapered section first cross-sectional shape extends along a length of the tapered section from said first end to the second cross-sectional shape at said second end, said first cross-sectional shape including a shape other than a square shape and said second cross-sectional shape including a circular shape.

* * * * *